United States Patent [19]

Yoneda et al.

[11] Patent Number: 5,606,116
[45] Date of Patent: Feb. 25, 1997

[54] CHROMATOGENOUS TESTING SYSTEM FOR URINALYSIS

[75] Inventors: Yuko Yoneda; Toshiyuki Itooka, both of Toyama, Japan

[73] Assignee: Kabushiki Kaisha Nippon Gene, Tokyo, Japan

[21] Appl. No.: 550,467

[22] Filed: Oct. 30, 1995

[30] Foreign Application Priority Data

Oct. 29, 1994 [JP] Japan ................... 6-014995 U

[51] Int. Cl.$^6$ ............... A01N 1/02; G01N 33/52; C12Q 1/68
[52] U.S. Cl. ................ 73/61.52; 73/61.54; 422/68.1; 422/70; 436/74; 436/162; 436/108; 210/658
[58] Field of Search ................ 73/61.52, 61.54, 73/61.53; 422/68.1, 70; 436/74, 161, 162, 175, 108; 210/658

[56] References Cited

U.S. PATENT DOCUMENTS

| | | | |
|---|---|---|---|
| 3,912,655 | 10/1975 | Shukla et al. | 252/408 |
| 4,066,403 | 1/1978 | Bruschi | 23/230 B |
| 4,703,017 | 10/1987 | Campbell et al. | 436/501 |
| 4,861,711 | 8/1989 | Friesen et al. | 436/7 |
| 4,960,691 | 10/1990 | Gordon et al. | 435/6 |
| 4,966,784 | 10/1990 | Tanaka et al. | 427/2 |
| 5,171,528 | 12/1992 | Wardlaw et al. | 422/56 |
| 5,186,894 | 2/1993 | Katsuyama | 422/56 |
| 5,258,163 | 11/1993 | Krause et al. | 422/58 |
| 5,281,393 | 1/1994 | Kurchacova et al. | 422/56 |
| 5,350,510 | 9/1994 | Partney, Jr. | 210/198.3 |
| 5,350,675 | 9/1994 | Makino et al. | 435/11 |
| 5,356,782 | 10/1994 | Moorman et al. | 435/7.9 |

FOREIGN PATENT DOCUMENTS 1-503174  10/1989  Japan .
7-13640   2/1995   Japan .

Primary Examiner—Hezron E. Williams
Assistant Examiner—J. David Wiggins
Attorney, Agent, or Firm—Browdy and Neimark

[57] ABSTRACT

A testing system for urinalysis is provided comprising a support member which carries a developing phase, a reagent carrying means, a urine applying section, and a urine-reagent developing area. In order to prevent inaccurate test results which may result from splashing the sample onto the device, a water-repellent agent is coated onto both sides of the reagent phase and the urine-reagent developing phase, as well as onto both sides of the support member where the reagent phase and the urine-reagent developing phase are provided. The water repellent agent is solidified, and a transparent resin film is attached to the upper surfaces of the reagent phase and the urine-reagent developing phase. In another embodiment, instead of the combination of a water repellent agent and a transparent resin film attached to the upper surfaces of the reagent phase and the urine-reagent developing phase, the device is enclosed in an envelope-like or cylindrical transparent resin film or container.

4 Claims, 1 Drawing Sheet

CHROMATOGENOUS TESTING SYSTEM FOR URINALYSIS

BACKGROUND OF THE INVENTION

The present invention relates to a chromatogenous testing system for urinalysis, in which both sides and the upper surface of a reagent phase and a urine-reagent developing phase as well as both sides of a support member where the reagent phase and the urine-reagent developing phase are attached are designed as waterproof so that development of chromatogenous solvent is not hindered even when the urine to be tested is directly applied to sectors where the chromatogenous solvent is developing.

In a conventional chromatogenous testing system for urinalysis, after the urine to be tested is collected into a container such as a urine cup, only a urine applying sector of the chromatogenous testing system is immersed in the urine or the urine to be tested is taken into a syringe, and it is then applied to the urine applying sector.

In the conventional chromatogenous testing system as described above, when the urine specimen is placed onto the urine applying sector at one end of the system, the urine to be tested often splashes, and the splashed urine directly invades the developing sector of the urinalysis (hereinafter referred as "urine-reagent" because the urine is mixed here with the reagent in the chromotography system on the way of development), which advances and develops continuously from the urine applying sector to a developing phase through a reagent phase. As a result, the development of the urine-reagent from the urine applying sector is hindered, and it is not always possible to obtain accurate reaction results.

Some of the testing system is designed as waterproof, but it is not possible to prevent infiltration of the urine to be tested from both sides of a reagent phase layer, and accurate reaction results cannot be obtained.

For this reason, the urine to be tested must be put into the urine testing unit using a urine cup or a syringe, and this means can result in a troublesome procedure.

SUMMARY OF THE INVENTION

It is an object of the present to provide a testing system, in which such troublesome procedure can be eliminated and the adverse effect of the splashed urine when the urine is applied to the urine applying sector can be avoided.

According to the present invention, the development of the urine reagent is not hindered by the splashed urine even when the urine to be tested is directly applied to the urine applying sector and accurate reaction results can be obtained. In the following, description will be given on the present invention referring to the drawings.

DETAILED DESCRIPTION OF THE PREFERRED EMBODIMENTS

Figure 1:
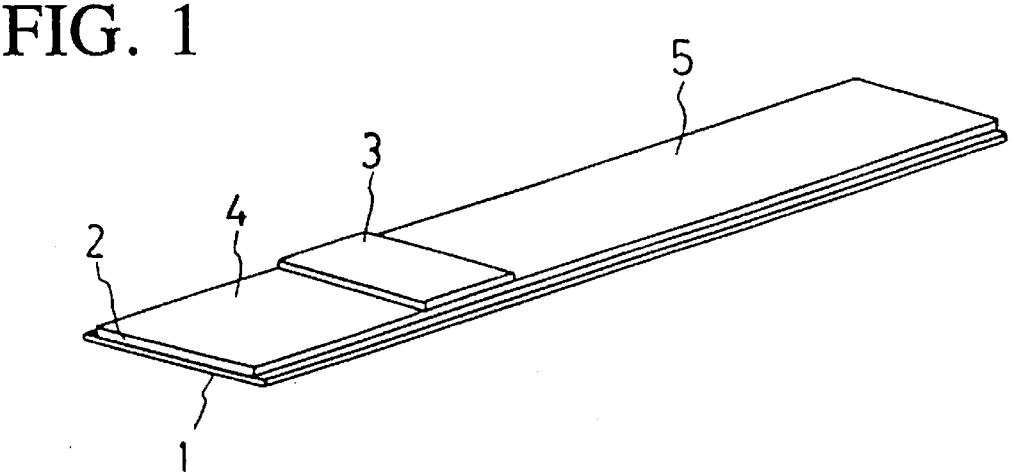
FIG. 1 is a perspective view of a conventional type chromatogenous testing system.

In the figures, reference numeral 1 represents a support member, 2 represents a developing phase, 3 a reagent phase, 4 urine applying sector, 5 a urine-reagent developing phase, 6 a water repellent agent, 7 a transparent resin film, and 8 represents an envelope-like or cylindrical transparent resin film or container.

FIG. 1 is a perspective view of a conventional chromatogenous testing system, in which a developing phase (2) is provided on upper surface of a support member (1), and a reagent phase (3) is positioned on a sector closer to one end of the developing phase (2). With the reagent phase (3) as a border, a urine applying sector (4) is positioned in the sector closer to one end of the developing phase (2), and the remaining long sector is used as the urine-reagent developing phase (5). The urine applying sector (4) is immersed in the urine to be tested which has been collected in a urine cup or the urine to be tested sucked into a syringe is put onto the urine applying sector (4) to perform the test.

EXAMPLE 1

Figure 2:
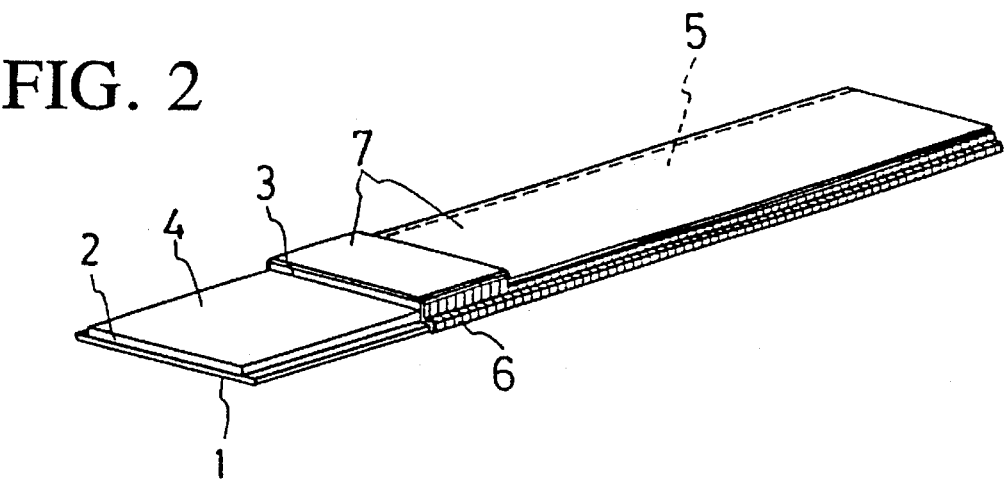
FIG. 2 is a perspective view of a first embodiment of the present invention.

Next, description will be given on Example 1 of the chromatogenous testing system of the present invention, referring to the perspective view of FIG. 2. In addition to the conventional type testing system, a water repellent agent (6) is coated on both sides of the reagent phase (3) and the urine-reagent developing phase (5) as well as on both sides of the support member (1) where the reagent phase (3) and the urine-reagent developing phase (5) are provided. Then, the water repellent agent is solidified by irradiating heat, ultraviolet ray, infrared ray, etc., and a transparent resin film (7) is attached on upper surfaces of the reagent phase (3) and the urine-reagent developing phase (5).

EXAMPLE 2

Figure 3:
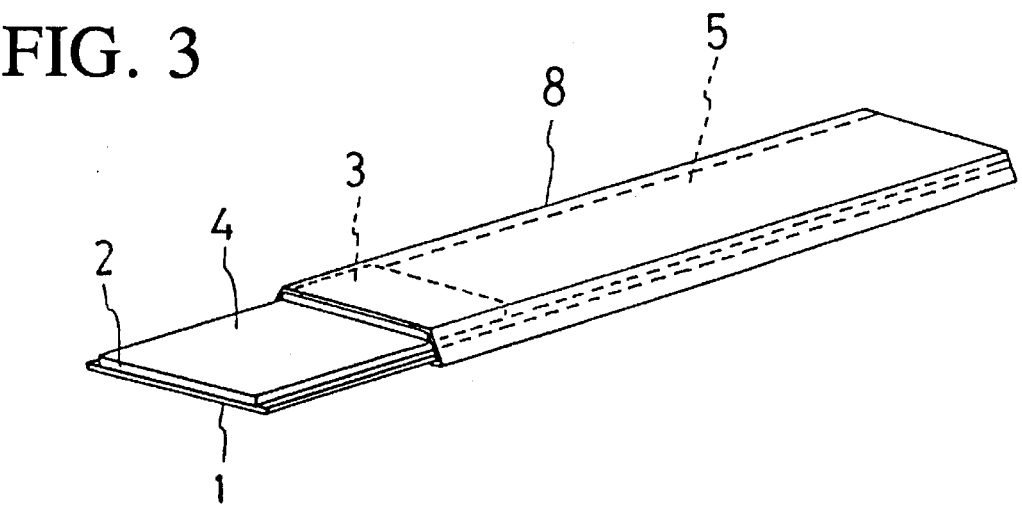
FIG. 3 is a perspective view of a second embodiment of the present invention.

Example 2 of the chromatogenous testing system of the present invention is described in connection with the perspective view of FIG. 3. In addition to the conventional testing system, the support member (1) with the reagent phase (3) and the urine-reagent developing phase (5) provided on it is accommodated in an envelope-like or cylindrical transparent resin film or container (8).

If the envelope-like or cylindrical transparent resin film or container (8) is made of a heat shrinkable resin, the reagent phase (3) and the urine-reagent developing phase (5) as well as the support member (1) can be enclosed within this heat shrinkable resin. Once heat is externally applied, the heat shrinkable resin shrinks around the reagent phase, urine-reagent developing phase and support member so that the heat shrinkable resin fits tightly around the phases and does not fall off during use.

Because the testing system of the present invention is designed as described above, even when the urine to be tested is directly applied to the urine applying sector (4), splashed urine is repelled by the water repellent agent (6) and transparent resin film (7) or by the envelope-like or cylindrical transparent resin film or container (8), and the splashed urine is not infiltrated or contaminating to the reagent phase (3) or the urine-reagent developing phase (5). As a result, the urine-reagent in the urine-reagent developing phase(5) is normally developed and accurate reaction results can be obtained. Also, any troublesome procedure that results due to use of a urine cup or syringe can be eliminated.

What we claim are:

1. A testing system for urinalysis performed by thin layer chromatography techniques, comprising:

a support member;

a urine applying sector;

a reagent phase layer;

a urine-reagent developing phase layer; and protective means, applied onto the edges and the outer surfaces of said reagent phase layer and said urine-reagent developing phase layer, for making said edges and outer surfaces waterproof.

2. A testing system according to claim 1, wherein said protective means comprises a transparent resin film or container which encloses said edges and outer surfaces of said reagent phase layer and said urine-reagent developing phase layer.

3. A testing system according to claim 1, wherein said protective means comprises a coating of water repellent agent which is solidified.

4. A testing system according to claim 1, wherein said protective means comprises a transparent resin film layer which is attached to the outer surfaces of said layers.

* * * * *